United States Patent
Varga et al.

(10) Patent No.: US 6,852,127 B2
(45) Date of Patent: Feb. 8, 2005

(54) METHOD OF IMPLANTING AN INTERVERTEBRAL SPACER

(75) Inventors: Peter Pal Varga, Budapest (HU); James A. Ogilvie, Edina, MN (US)

(73) Assignee: Ortho Development Corporation, Draper, UT (US)

( * ) Notice: Subject to any disclaimer, the term of this patent is extended or adjusted under 35 U.S.C. 154(b) by 0 days.

(21) Appl. No.: 10/055,783

(22) Filed: Jan. 22, 2002

(65) Prior Publication Data

US 2002/0065558 A1 May 30, 2002

Related U.S. Application Data

(62) Division of application No. 09/592,072, filed on Jun. 12, 2000, now Pat. No. 6,579,318.

(51) Int. Cl.[7] .............................. A61F 2/44; A61F 2/46; A61B 17/88
(52) U.S. Cl. .................................... 623/17.11; 623/908
(58) Field of Search ................ 606/102, 61; 623/17.11, 623/17.16, 17, 908

(56) References Cited

U.S. PATENT DOCUMENTS

| 4,479,491 A | 10/1984 | Martin |
| 4,627,853 A | 12/1986 | Campbell et al. |
| 4,678,470 A | 7/1987 | Nashef et al. |
| 4,714,469 A | 12/1987 | Kenna |
| 4,834,757 A | * 5/1989 | Brantigan ............... 623/17.11 |
| 4,863,477 A | 9/1989 | Monson |
| 4,904,261 A | 2/1990 | Dove |
| 4,932,969 A | 6/1990 | Frey et al. |

(List continued on next page.)

FOREIGN PATENT DOCUMENTS

| DE | 26 49 042 C2 | * 9/1978 | .................. 606/61 |
| DE | 299 01 611 U1 | * 4/1999 | ............. A61F/2/46 |

(List continued on next page.)

OTHER PUBLICATIONS

Péter Pál Varga, "Dekompresszö és rigid stabilizálás (fusio)." *Lumbalis spinalis stenosis*, pp. 98–113. 1995. (with English translation).

*Primary Examiner*—David H. Willse
(74) *Attorney, Agent, or Firm*—Clayton, Howarth & Cannon, P.C.

(57) ABSTRACT

An intervertebral spacer adapted for implanting between adjacent vertebral bodies of a human spine as a load-bearing replacement for a spinal disc. The spacing member includes an external, non-porous, concavo-convex contour with respect to one dimension of the spacing member. The spacing member is preferably constructed from a rigid, non-resilient load-bearing material that is incapable of elastic deformation. The spacing member is inserted with the aid of a sheathed trocar device that is releasably attached to the spacer, to enable implantation and selective positioning of the spacer by the surgeon from the posterior side of the spine, without the need to retract the dural nerve or the posterior longitudinal ligament.

32 Claims, 4 Drawing Sheets

U.S. PATENT DOCUMENTS

| | | |
|---|---|---|
| 4,950,296 A | 8/1990 | McIntyre |
| 5,053,049 A | 10/1991 | Campbell |
| 5,071,437 A | 12/1991 | Steffee |
| 5,092,893 A | 3/1992 | Smith |
| 5,123,926 A | 6/1992 | Pisharodi |
| 5,171,281 A | 12/1992 | Parsons et al. |
| 5,192,326 A | 3/1993 | Bao et al. |
| 5,192,327 A | 3/1993 | Brantigan |
| 5,275,954 A | 1/1994 | Wolfinbarger et al. |
| 5,306,303 A | 4/1994 | Lynch |
| 5,306,308 A | 4/1994 | Gross et al. |
| 5,306,309 A | 4/1994 | Wagner et al. |
| 5,344,459 A | 9/1994 | Swartz |
| 5,425,772 A | 6/1995 | Brantigan |
| 5,458,638 A | 10/1995 | Kuslich et al. |
| 5,458,643 A | 10/1995 | Oka et al. |
| 5,514,180 A | 5/1996 | Heggeness et al. |
| 5,534,028 A | 7/1996 | Bao et al. |
| 5,534,030 A | 7/1996 | Navarro et al. |
| 5,545,229 A | 8/1996 | Parsons et al. |
| 5,556,379 A | 9/1996 | Wolfinbarger |
| 5,571,192 A | 11/1996 | Schönhöffer |
| 5,593,409 A | 1/1997 | Michelson |
| 5,609,637 A | 3/1997 | Biedermann et al. |
| 5,645,598 A | 7/1997 | Brosnahan, III |
| 5,653,762 A | 8/1997 | Pisharodi |
| 5,658,337 A | 8/1997 | Kohrs et al. |
| 5,674,295 A | 10/1997 | Ray et al. |
| 5,676,702 A | 10/1997 | Ratron |
| 5,702,449 A | 12/1997 | McKay |
| 5,702,451 A | 12/1997 | Biedermann et al. |
| 5,702,455 A | 12/1997 | Saggar |
| 5,720,748 A | 2/1998 | Kuslich et al. |
| 5,722,977 A | 3/1998 | Wilhelmy |
| 5,725,579 A | 3/1998 | Fages et al. |
| 5,728,159 A | 3/1998 | Stroever et al. |
| 5,741,253 A | 4/1998 | Michelson |
| 5,755,798 A | 5/1998 | Papavero et al. |
| 5,766,252 A | 6/1998 | Henry et al. |
| 5,766,253 A | 6/1998 | Brosnahan, III |
| 5,776,199 A | 7/1998 | Michelson |
| 5,785,710 A | 7/1998 | Michelson |
| 5,797,871 A | 8/1998 | Wolfinbarger, Jr. |
| 5,814,084 A | 9/1998 | Grivas et al. |
| 5,820,581 A | 10/1998 | Wolfinbarger, Jr. |
| 5,824,094 A | 10/1998 | Serhan et al. |
| 5,860,973 A | 1/1999 | Michelson |
| 5,861,041 A | 1/1999 | Tienboon |
| 5,865,845 A | 2/1999 | Thalgott |
| 5,876,457 A | 3/1999 | Picha et al. |
| 5,888,222 A | 3/1999 | Coates et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,897,556 A | 4/1999 | Drewry et al. |
| 5,897,593 A | 4/1999 | Kohrs et al. |
| 5,961,554 A | 10/1999 | Janson et al. |
| 5,972,368 A | 10/1999 | McKay |
| 5,989,289 A | 11/1999 | Coates et al. |
| 6,022,376 A | 2/2000 | Assell et al. |
| 6,045,580 A | 4/2000 | Scarborough et al. |
| 6,059,829 A | 5/2000 | Schläpfer et al. |
| 6,080,158 A | 6/2000 | Lin |
| 6,093,205 A | 7/2000 | McLeod et al. |
| 6,096,081 A | 8/2000 | Grivas et al. |
| 6,117,174 A | 9/2000 | Nolan |
| 6,132,465 A | 10/2000 | Ray et al. |
| 6,139,579 A | 10/2000 | Steffee et al. |
| 6,143,031 A | 11/2000 | Knothe et al. |
| 6,143,032 A | 11/2000 | Schafer et al. |
| 6,143,033 A | 11/2000 | Paul et al. |
| 6,146,422 A | 11/2000 | Lawson |
| 6,149,651 A | 11/2000 | Drewry et al. |
| 6,156,067 A | 12/2000 | Bryan et al. |
| 6,159,244 A | 12/2000 | Suddaby |
| 6,162,252 A | 12/2000 | Kuras et al. |
| 6,179,873 B1 | 1/2001 | Zientek |
| 6,179,874 B1 | 1/2001 | Cauthen |
| 6,210,412 B1 | 4/2001 | Michelson |
| 6,217,579 B1 | 4/2001 | Koros |
| 6,235,059 B1 | 5/2001 | Benezech et al. |
| 6,245,072 B1 | 6/2001 | Zdeblick et al. |
| 6,245,108 B1 | 6/2001 | Biscup |
| 6,258,125 B1 | 7/2001 | Paul et al. |
| 6,261,586 B1 | 7/2001 | McKay |
| 6,264,655 B1 | 7/2001 | Pisharodi |
| 6,264,656 B1 | 7/2001 | Michelson |
| 6,277,149 B1 | 8/2001 | Boyle et al. |
| 6,296,641 B2 | 10/2001 | Burkhead et al. |
| 6,296,647 B1 | 10/2001 | Robioneck et al. |
| 6,302,914 B1 | 10/2001 | Michelson |
| 6,306,170 B2 | 10/2001 | Ray |
| 6,309,421 B1 | 10/2001 | Pisharodi |
| 6,315,795 B1 | 11/2001 | Scarborough et al. |
| 6,315,797 B1 | 11/2001 | Middleton |
| 6,387,130 B1 | 5/2002 | Stone et al. |
| 6,402,785 B1 | 6/2002 | Zdeblick et al. |
| 6,648,915 B2 * | 11/2003 | Sazy ........................ 623/17.11 |
| 2001/0000532 A1 | 4/2001 | Michelson |
| 2001/0001129 A1 | 5/2001 | McKay et al. |

FOREIGN PATENT DOCUMENTS

| | | | |
|---|---|---|---|
| DE | 19710392 C1 | 7/1999 | |
| EP | 0 538 183 A1 | 4/1993 | |
| EP | 0 599 419 | 6/1994 | |
| FR | 2736537 A1 | 1/1997 | |
| JP | 5-208029 A * | 8/1993 | .................. 623/17 |
| JP | 9-122160 A * | 5/1997 | ............. A61F/2/44 |
| WO | WO 94/26213 | 11/1994 | |
| WO | WO 97/06753 | 2/1997 | |
| WO | WO 97/15247 | 5/1997 | |
| WO | WO 98/17209 | 4/1998 | |
| WO | WO 98/55052 | 12/1998 | |
| WO | WO 98/56319 | 12/1998 | |
| WO | WO 98/56433 | 12/1998 | |

* cited by examiner

METHOD OF IMPLANTING AN INTERVERTEBRAL SPACER

CROSS-REFERENCE TO RELATED APPLICATIONS

This application is a division of co-pending U.S. patent application Ser. No. 09/592,072, filed Jun. 12, 2000 now U.S. Pat. No. 6,579,318, entitled "INTERVERTEBRAL SPACER" which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to an intervertebral spacer, and more particularly, but not necessarily entirely, to a interbody spacing system for accomplishing enhanced intervertebral fusion between adjacent vertebral bodies of a human spine.

2. Description of Related Art

The human spine is a complex, sophisticated mechanical system. The vertebrate spine operates as a structural member, providing structural support for the other body parts. A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae.

The anulus of the disc forms the disc perimeter, and is a tough, outer fibrous ring that binds adjacent vertebrae together. The fiber layers of the anulus include fifteen to twenty overlapping plies, which are inserted into the superior and inferior vertebral bodies at roughly a 40 degree angle in both directions. This causes bi-directional torsional resistance, as about half of the angulated fibers will tighten when the vertebrae rotate in either direction.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. U.S. Pat. No. 4,863,477 (granted Sep. 5, 1989 to Monson) discloses a resilient spinal disc prosthesis intended to replace the resiliency of a natural human spinal disc. U.S. Pat. No. 5,192,326 (granted Mar. 9, 1993 to Bao et al.) teaches a prosthetic nucleus for replacing just the nucleus portion of a human spinal disc.

In other cases it is desired to fuse the adjacent vertebrae together after removal of the disc, sometimes referred to as "intervertebral fusion" or "interbody fusion."

In cases of intervertebral fusion, it is known to position a spacer centrally within the space where the spinal disc once resided, or to position multiple spacers within that space. Such practices are characterized by certain disadvantages, including a disruption in the natural curvature of the spine. For example, the vertebrae in the lower "lumbar" region of the spine reside in an arch referred to in the medical field as having a sagittal alignment. The sagittal alignment is compromised when adjacent vertebral bodies that were once angled toward each other on their posterior side become fused in a different, less angled orientation relative to one another.

Another disadvantage of known spacing techniques and intervertebral spacers are the additional surgical complications that arise in the use of multiple spacers in a single disc space. In such cases, surgeons will often first perform a posterior surgery to remove the affected disc and affix posterior instrumentation to the posterior side of the vertebrae to hold the posterior portions of the vertebrae in a desired position. Placement of the multiple spacers is often too difficult to accomplish from the posterior side of the patient, at least without causing with undue trauma to the patient, because a surgeon would need to retract the dura nerve as well as the anterior longitudinal ligament, thereby increasing damage, pain and morbidity to the patient. Surgeons have therefore often chosen to turn the patient over after completing the posterior surgical portion, to perform an anterior operative procedure, through the patient's belly, in order to insert multiple spacers between the vertebrae from the anterior side instead of from the posterior side.

U.S. Pat. No. 5,961,554 (granted Oct. 5, 1999 to Janson et al.) illustrates a spacer having a high degree of porosity throughout, for enhanced tissue ingrowth characteristics. This patent does not address the problem of compromising the sagittal alignment, or of increased pain and trauma to the patient by implantation of multiple spacers in a single disk space.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is therefore an object of the present invention to provide an intervertebral spacing system that does not require an additional, anterior surgical procedure.

It is another object of the present invention, in accordance with one aspect thereof, to provide such an intervertebral spacing system by which sagittal alignment of the spine is restored.

It is a further object of the present invention, in accordance with one aspect thereof, to provide such an intervertebral spacing system that can accommodate a larger host-graft interface between adjacent vertebral bodies.

It is an additional object of the present invention, in accordance with one aspect thereof, to provide such an intervertebral spacing system in which bone grafting material is loaded in compression between adjacent vertebral bodies of the spine.

It is yet another object of the present invention, in accordance with one aspect thereof, to provide such an intervertebral spacing system that does not require retraction of the dural nerve, or of the anterior or posterior longitudinal ligaments, for implantation of the spacer.

The above objects and others not specifically recited are realized in a specific illustrative embodiment of an intervertebral spacer adapted for implanting between adjacent vertebral bodies of a human spine as a load-bearing replacement for a spinal disc. The spacing member includes an external, non-porous, concavo-convex contour with respect to one dimension of said spacing member. The spacing member is preferably constructed from a rigid, non-resilient load-bearing material that is incapable of elastic deformation. The spacing member is inserted with the aid of a sheathed trocar device that is releasably attached to the spacer, to enable implantation and selective positioning of the spacer by the surgeon from the posterior side of the spine, without the need to retract the dural nerve or the posterior longitudinal ligament.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE INVENTION

Figure 1:
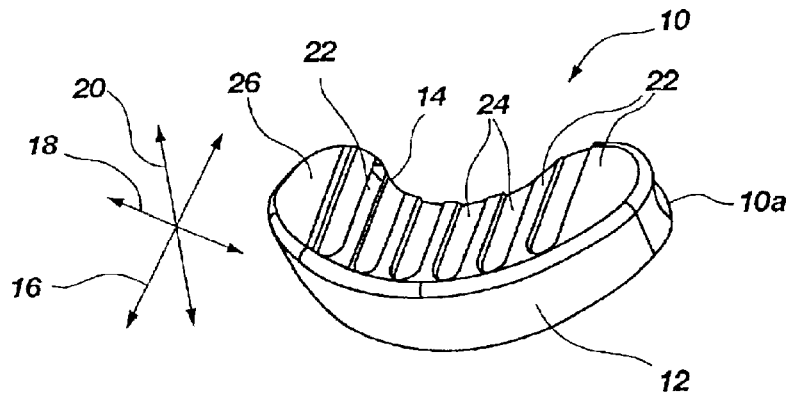
FIG. 1 is a perspective view of an intervertebral spacer, made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the apparatus and methods of the present invention are described further, it is to be understood that the invention is not limited to the particular configurations, process steps, and materials disclosed herein as such configurations, process steps, and materials may vary somewhat. It is also to be understood that the terminology employed herein is used for the purpose of describing particular embodiments of the invention only, and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as a suggestion or admission that the inventors are not entitled to antedate such disclosure by virtue of prior invention.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

Applicants have discovered that several of the disadvantages of the prior art spinal disc replacement systems can be minimized, or even eliminated, by the use of a cashew-shaped interbody spacer having a tapered external shape, placing it is far anteriorly as possible between adjacent vertebral bodies, filling in the remaining posterior space with bone graft material, and applying compression to posterior portions of the vertebral bodies to load the bone graft in compression and restore sagittal alignment.

Referring now to FIGS. 1–4, there is shown a spacing member, referred to also herein as an intervertebral spacer or an interbody spacer, designated generally at 10.

Figure 5:
FIG. 5 is side view of a pair of adjacent vertebral bodies from the lumbar region of a human spine.
Figure 6:
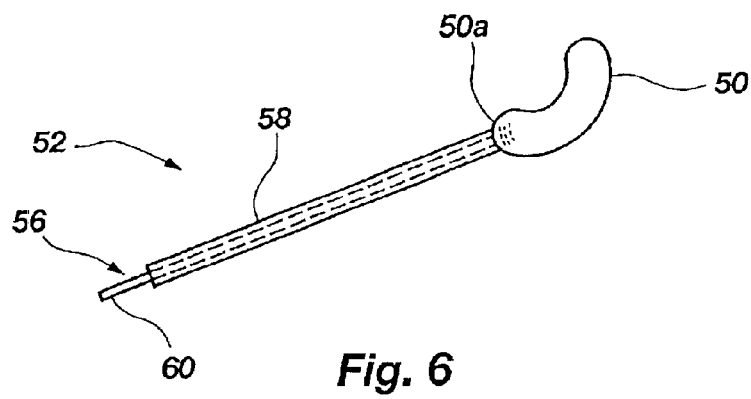
FIG. 6 is a schematic view of a sheathed trocar device releasably attached to a trial spacer shaped similarly to the intervertebral spacer of FIG. 1, in accordance with the principles of the present invention.
Figure 7:
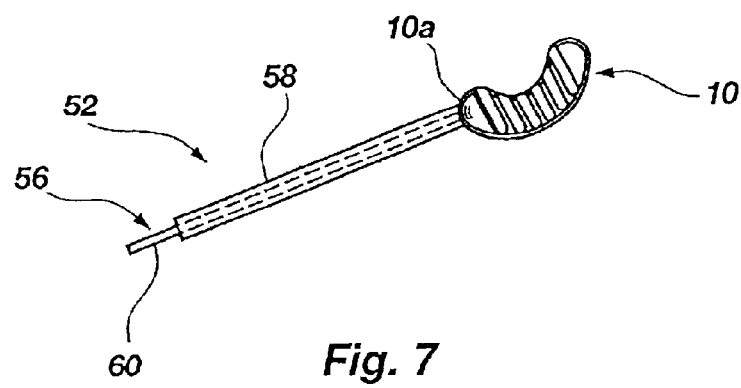
FIG. 7 is a schematic view of a sheathed trocar device releasably attached to the intervertebral spacer of FIG. 1, in accordance with the principles of the present invention.

Briefly stated, the spacer 10 is utilized, along with autogenous bone grafting material, to replace a diseased or damaged spinal disc. Referring now to FIGS. 5–7, the procedure is implemented by making an incision 32 in the anulus 34 connecting adjacent vertebral bodies 31. The spinal disc (not shown) is surgically removed from the incision 32, after which the spacer 10 is placed through the incision 32 into position between the vertebral bodies 31. The spacer is preferably placed with its convex, anterior sidewall 12 facing anteriorly, and with its concave, posterior sidewall 14 facing posteriorly. Bone grafting material is placed through the incision 32 to reside behind the spacer 10, after which posterior instrumentation is attached to pedicle areas 34 to force the vertebral bodies 31 together in compression, as illustrated schematically in FIG. 8D and more particularly in FIG. 9.

The unique aspects and procedures relating to the spacer 10 will now be explained in more detail. Some of the key features of the invention comprise the size, shape and placement of spacer 10. The spacer 10 is preferably made of titanium, thus having a non-porous quality with a preferably smooth finish. The spacer 10 could also be made of ceramic, or any other suitable material that is inert and biologically compatible. The spacer 10 is thus constructed from a rigid, non-resilient load-bearing material, one that is preferably incapable of elastic deformation. The spacer 10, by its anterior, convex sidewall 12 and its posterior, concave sidewall 14, has thereby a concavo-convex contour with respect to one dimension.

It is to be understood that the concept of an object having a concavo-convex contour with respect to one dimension of the object, as referred to herein, shall not require the concave and convex sides of the object to be parallel to one another, although such is preferred. The concept does however refer to a dimension in which the concave and convex sides of the object are at least partially facing the direction of that dimension, as indicated by the dimension 16 of FIG. 1 in relation to the spacer 10. It is also to be understood that the concept of an object being concavo-convex in a single dimension shall thereby include an object that has concave and convex sides 14 and 12 in a horizontal dimension 16, even though those very same sides are linear in a vertical dimension 20 at all points, such as in the case of the spacer 10 shown in FIG. 1. For example, the spacer 10 is concavo-convex in the anterior-posterior direction 16, though not in a medial-lateral direction 18 or vertical direction 20.

Figure 3:
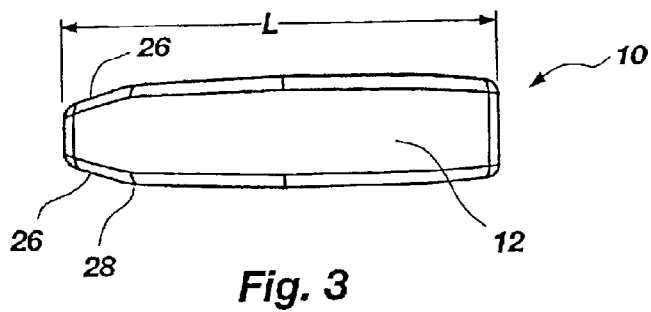
FIG. 3 is a frontal view of the intervertebral spacer of FIGS. 1 and 2.
Figure 4:
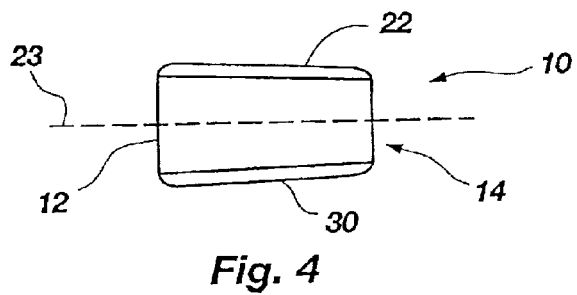
FIG. 4 is a side view of the intervertebral spacer of FIGS. 1, 2 and 3.

The upper surface 22 of the spacer 10 is preferably a planer, discontinuous surface having a plurality of spaced-apart elongate recesses 24, with preferably a corner point 28 whereby one side 26 of the spacer 10 begins tapering in the medial-lateral direction 18, as shown most clearly in FIG. 3. The primary taper of the spacer 10 occurs in the anterio-to-posterior direction 16, in that the spacer 10 narrows in thickness in a continuous manner along substantially the entire spacer 10 as shown most clearly in FIG. 4. The upper surface 22 and lower surface 30 form an acute angle relative to a horizontal plane 23, the angle being with a range of preferably two to eight degrees, most preferably four degrees. The entire taper is therefore most preferably an eight degree total taper, with four degrees of taper resulting from the upper surface 22 and the other four degrees of taper resulting from the lower surface 30.

Figure 2:
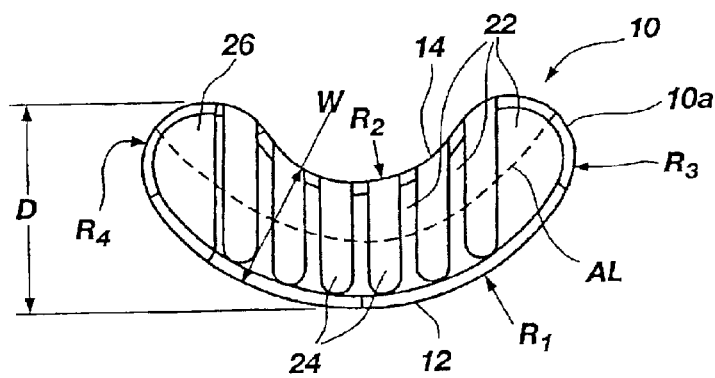
FIG. 2 is a plan view of the intervertebral spacer of FIG. 1.

As shown most clearly in FIG. 2, the spacer 10 has an arc-length AL that is preferably 1.218 inches, a width W that is preferably 0.320 inches, a depth D that is preferably 0.532 inches, an inner radius $R_2$ that is 0.271 inches, an outer radius $R_1$ that is preferably 0.591 inches, and side radii $R_3$ and $R_4$ that are each preferably 0.160 inches.

The anterior, convex sidewall 12 and the posterior, concave sidewall 14 of the spacer 10 are each preferably linear in the vertical dimension 20, and are most preferably parallel relative to one another.

The primary goal in intervertebral fusion are immobilization of the affected vertebrae, restoration of the spinal disc space and sagittal alignment, and to provide an environment for bony fusion between vertebral bodies. Applicants have discovered that these goals are most effectively accomplished by the mechanical principle of a cantilever. Using the spacer 10 as a compression point, a cantilever is constructed within the disc space as shown most clearly in FIG. 8D. The procedure for accomplishing this is as follows.

Figure 8A:
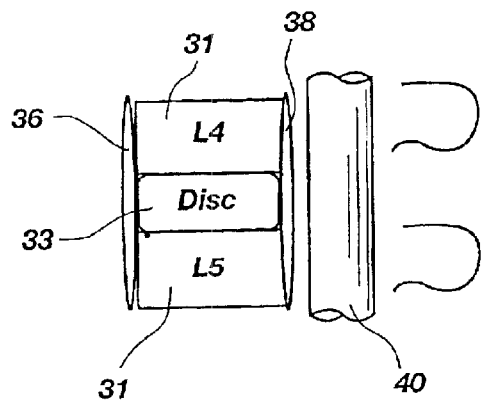
FIGS. 8A–8D illustrate a schematic progression of the placement of the intervertebral spacer of FIG. 1 between vertebral bodies of a human spine.

FIG. 8A is a schematic side, internal view of the vertebral bodies 31 indicated in FIG. 5. The spinal disc 33 resides between the vertebral bodies 31, all of which reside between the anterior longitudinal ligament (ALL) 36 and the posterior longitudinal ligament (PLL) 38. The dural nerve (Dura) 40 resides posteriorly to the vertebral bodies 31 and the PLL 38.

Figure 8B:
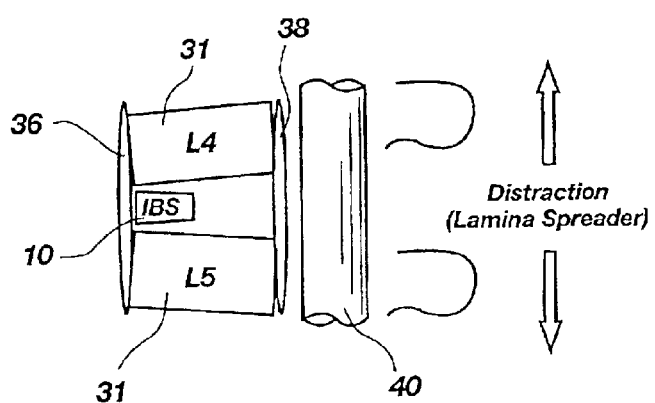
Figure 8C:
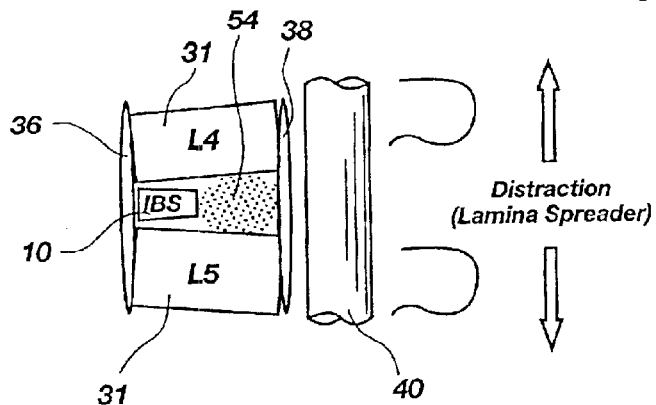
Figure 9:
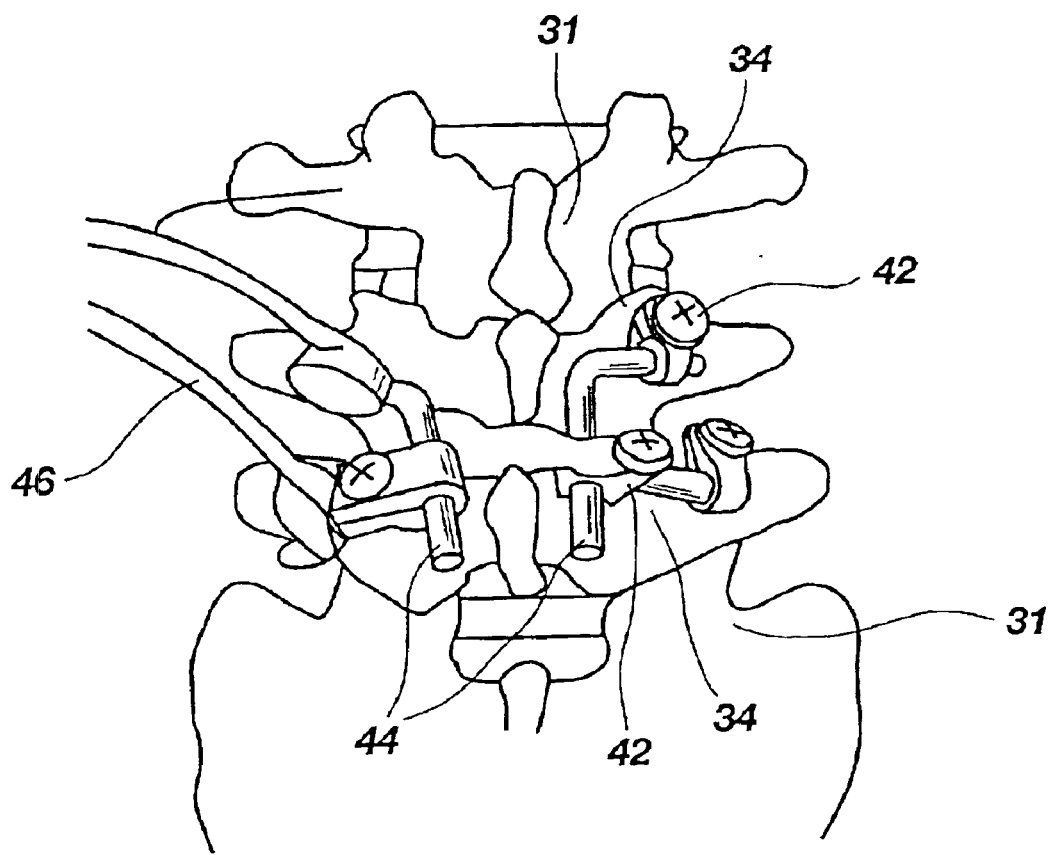
FIG. 9 illustrates posterior instrumentation by which compression is applied to the posterior sides of a paid of adjacenet vertebral bodies of a human spine.

Referring now to FIG. 8B and FIG. 9, posterior access to the spine of the patient (not shown) is accomplished. Posterior instrumentation, preferably pedicle screws 42 (FIG. 9), are affixed to posterior pedicle portions 34 of the vertebral bodies 31. The associated rods 44 and structure interconnecting the rods 44 with the pedicle screws 42 are not affixed until later on in the procedure. A posterior portion of the lower vertebral body involved in the fusion, namely, the left inferior articular facet, is removed and saved for future autogenous bone grafting. A lamina spreader (not shown, but indicated in FIGS. 8B and 8C), is placed between the spinous processes 35 (shown in FIG. 5), and is operated to spread the adjacent vertebral bodies 31 apart. The anterior longitudinal ligament 36 and posterior longitudinal ligament 38 are left intact and need not be retracted.

After coagulation of the veins (not shown), the incision 32 (FIG. 5) is made, preferably with a #15 scalpel, or any suitable surgical instrument, in a side section of the anulus 37. The disc 33 is then detached from the vertebral end plates (not shown) with the proper surgical instrumentation, and is removed through the incision 32. Care is taken not to violate the bony vertebral end plate, which would cause excessive bleeding and compromise the resistance to axial load when the spacer 10 is inserted.

When as much disc material has been removed as can safely be accomplished, a trial spacer 50 is used to determine the correct spacer size. The trial spacer 50 preferably has the same shape as the spacer 10, both of which are part of a set having various sizes, except that the trial spacer 50 does not include the recesses 24. The trial spacer 50 is inserted into the incision 32 with a sheathed trocar device 52. The main purpose of trial spacer 50 is to evaluate a snugness of fit of said trial spacer 50 as it resides between the adjacent vertebral bodies 31, which enables the surgeon to determine a spacer size thereby. The trial spacer 50 may also have sharp edging, and is useable to clear away any remaining unwanted tissue.

When the spacer size has been determined, a bone graft is prepared, preferably autogenous bone graft material 54 as shown in FIG. 8C. Care is taken to remove all soft tissue from the autogenous bone, which will facilitate successful osseointegration of the graft. Additional bone can also be harvested from the spinous processes 35. The harvested autogenous bone is then passed through a bone mill (not shown) to form suitable bone grafting material as known and understood to those having ordinary skill in the art.

The spacer 10 is inserted through the incision 32 with the sheathed trocar device 52. The sheathed trocar device 52 includes a trocar rod 56 preferably slidably disposed within a hollow sheath 58. The trocar rod 56 and the hollow sheath 58 may moveably engaged with each other in any suitable manner.

Both the trial spacer 50 and the spacer 10 preferably include a female-threaded opening 50a and 10a formed therein, respectively, in which a male-threaded portion 57 of the trocar rod 56 may be releasably inserted. The trocar rod 56 may of course be releasably attached to the trial spacer 50 and spacer 10 in any other suitable manner. The trocar rod 56 has a longer length than the sheath member 58, such that a proximal portion 60 of the trocar rod 56 protrudes from the sheath member 58 when the trocar rod 56 is attached to the trial spacer 50 or the spacer 10.

The sheathed trocar device 52 accordingly provides an efficiently stabilized, releasable connection with the spacer 10. With the trocar rod 56 being attached directly to the spacer 10, the sheath member 58 provides additional support by abutting up against the spacer and contactably circumscribing the point of the attachment of the trocar rod 56 with the spacer 10, thereby providing additional stability and control over the positioning of the spacer 10.

The surgeon then selectively positions the spacer 10 within the space residing between the adjacent vertebral bodies 31, preferably as far anteriorly as possible and most preferably such that the spacer 10 resides in contact with the anterior longitudinal ligament 36.

With the spacer 10 in place, the bone grafting material 54 is placed through the incision 32 and into position between the adjacent vertebral bodies 31, such that said bone grafting material 54 resides posteriorly to the concave sidewall 14 of the spacer 10, and thus between the sidewall 14 and the posterior longitudinal ligament 38. A bone funnel (not shown) as known to those having ordinary skill in the field may be used to funnel morselized bone grafting material into the incision 32.

It is noted that the concavo-convex shape of the spacer 10, and the method of implantation with the spacer 10 residing as far anteriorly as possible, operates to provide a larger bone-graft interface between the adjacent vertebral bodies 31.

Figure 8D:
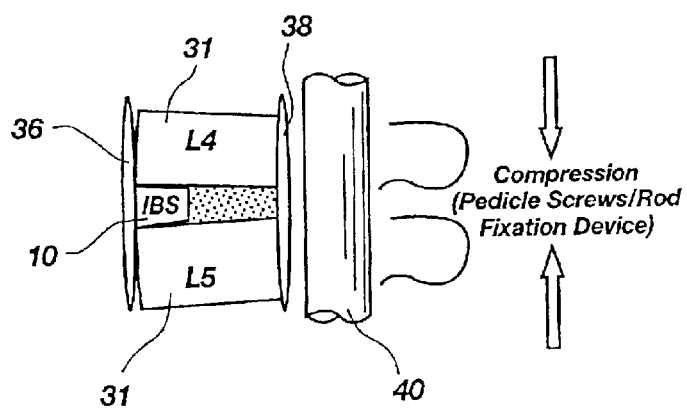

Referring now to FIG. 8D and FIG. 9, the lamina spreader is removed and the pedicle screws 42 are interconnected with the rods 44 as known in the field. Mild compression is applied by a compression instrument 46 to thereby slide rods 44 downwardly, after which the pedicle screws 42 are tightened to hold the rods 44 in place and maintain the compression. Further compression is applied as desired, with the result being illustrated schematically in FIG. 8D. The bone grafting material 54 is thereby loaded in compression by the posteriorly compressed adjacent vertebral bodies 31 as shown. After final inspection of the placement of the bone grafting material 54, routine closure of the wound is completed. The use of drains may be made at the discretion of the surgeon.

The spacer 10 thus operates to cause the adjacent vertebral bodies 31 to be suspended in the manner of a cantilever. The posterior compression provided by the pedicle screws 42 and rods 44, which may alternatively be provided by any other suitable holding structure, causes the adjacent vertebral bodies 31 to be brought closer together on their posterior side than on their anterior side, consistent with the natural sagittal alignment in which they were originally positioned, as understood by those having ordinary skill in the field.

It will be appreciated that the structure and apparatus of the trocar rod 56 and sheath 58 constitute a positioning means for enabling a surgeon to adjust a position of the spacer 10 when the spacer 10 resides between the adjacent intervertebral bodies 31. That structure is merely one example of a means for positioning the spacer 10, and it should be appreciated that any structure, apparatus or system for positioning which performs functions that are the same as, or equivalent to, those disclosed herein are intended to fall within the scope of a means for positioning, including those structures, apparatus or systems for positioning which are presently known, or which may become available in the future. Anything which functions the same as, or equivalently to, a means for positioning falls within the scope of this element.

In accordance with the features and combinations described above, a preferred method of implanting an artificial intervertebral disc includes:

(a) making an incision in an anulus of a human spinal column between adjacent vertebral bodies of said spinal column to thereby expose a space residing between said adjacent vertebral bodies;

(b) inserting a spacing member through the incision and into position between the adjacent vertebral bodies, and positioning said spacing member at an anterior location with respect to the spinal column such that more intervertebral space resides posteriorly to said spacing member than anteriorly thereto;

(c) applying compression to posterior portions of the adjacent vertebral bodies.

It is to be understood that the above-described arrangements are only illustrative of the application of the principles of the present invention. Numerous modifications and alternative arrangements may be devised by those skilled in the art without departing from the spirit and scope of the present invention and the appended are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of implanting an artificial intervertebral disc comprising:

(a) making an incision in an anulus of a human spinal column between adjacent vertebral bodies of said spinal column to thereby expose a space residing between said adjacent vertebral bodies;

(b) inserting a spacing member, with a tapered end of said spacing member first, through the incision and into position between the adjacent vertebral bodies, and positioning said spacing member at an anterior location with respect to the spinal column such that more intervertebral space resides posteriorly to said spacing member than anteriorly thereto;

(c) applying compression to posterior portions of the adjacent vertebral bodies.

2. The method of claim 1, further comprising:

(d) removing a natural human disc from the space, prior to part (b).

3. The method of claim 1, further comprising attaching an insertion instrument to said spacing member.

4. The method of claim 3, wherein attaching an insertion instrument to said spacing member comprises threading a trocar on said spacing member.

5. The method of claim 4, further comprising supporting said spacing member with a hollow sheath member, said trocar being slidably disposed within said hollow sheath member.

6. The method of claim 1, wherein part (c) further comprises compressing the posterior portions of the adjacent vertebral bodies toward each other to a degree sufficient to move said adjacent vertebral bodies into a sagittal alignment.

7. The method of claim 6, further comprising:
(e) attaching a holding means to the adjacent vertebral bodies for holding said adjacent vertebral bodies in the sagittal alignment to thereby inhibit said vertebral bodies from moving out of sagittal alignment.

8. The method of claim 7, wherein attaching holding means further comprising affixing pedicle screws to posterior pedicle portions of the vertebral bodies, and interconnecting rods with the pedicle screws.

9. The method of claim 1, wherein part (b) further comprises positioning the spacing member sufficiently anteriorly such that said spacing member resides in contact with an anterior longitudinal ligament of the spinal column.

10. The method of claim 1 further comprising removing a posterior portion of one of the vertebral bodies for autogenous bone grafting.

11. The method of claim 1 further comprising placing a lamina spreader between spinous processes to spread adjacent vertebral bodies apart.

12. The method of claim 11 further comprising removing said lamina spreader after said spacing member is in place and closing the incision.

13. The method of claim 1 further comprising preparing a bone graft from autogenous bone graft material.

14. The method of claim 13 further comprising harvesting autogenous bone and passing said autogenous bone through a mill to form said autogenous bone graft material.

15. The method of claim 1 wherein part (c) further comprises tightening pedicle screws to maintain said compression.

16. The method of claim 1, further comprising bringing the adjacent vertebral bodies closer together on a posterior side than on an anterior side.

17. A method of implanting an artificial intervertebral disc comprising:
(a) making an incision in an anulus of a human spinal column between adjacent vertebral bodies of said spinal column to thereby expose a space residing between said adjacent vertebral bodies;
(b) inserting a spacing member, with a tapered end of said spacing member first, through the incision and into position between the adjacent vertebral bodies, and positioning said spacing member at an anterior location with respect to the spinal column such that more intervertebral space resides posteriorly to said spacing member than anteriorly thereto;
(c) placing bone grafting material through the incision and into position between the adjacent vertebral bodies such that said bone grafting material resides between the spacing member and a posterior longitudinal ligament of the spinal column; and
(d) attaching a compression means to posterior portions of the adjacent vertebral bodies to thereby force said posterior portions of the adjacent vertebral bodies toward each other and thereby compress the bone grafting material, said compression means comprising pedicle screws and rod members intercoupling said screws.

18. The method of claim 17, wherein the bone grafting material comprises autogenous bone.

19. The method of claim 17, further comprising attaching a trocar to said spacing member.

20. The method of claim 17, wherein step (b) further comprises:

attaching a trocar to said spacing member, said trocar being slidably disposed within a hollow sheath member;

abutting the sheath member against the spacing member and contactably circumscribing a point of attachment of the trocar with the spacing member to provide stability and control over the positioning of the spacing member; and inserting said spacing member through the incision in an arcuate insertion path.

21. A method of implanting an artificial intervertebral disc comprising:
(a) inserting a spacing member, with a tapered end of said spacing member first, into position between adjacent vertebral bodies of a human spinal column, and positioning said spacing member at an anterior location with respect to the spinal column such that more intervertebral space resides posteriorly to said spacing member than anteriorly thereto; and
(b) applying compression to posterior portions of the adjacent vertebral bodies.

22. The method of claim 21, further comprising additional parts to be performed prior to part (b), said additional parts comprising:
(i) placing bone grafting material into position between the adjacent vertebral bodies such that said bone grafting material resides between the spacing member and a posterior longitudinal ligament of the spinal column; and
(ii) attaching a compression means to posterior portions of the adjacent vertebral bodies to thereby force said posterior portions of the adjacent vertebral bodies toward each other and thereby compress the bone grafting material, said compression means comprising pedicle screws and rod members intercoupling said screws.

23. The method of claim 22, further comprising:

attaching a trocar to said spacing member, said trocar being slidably disposed within a hollow sheath member;

abutting the sheath member against the spacing member and contactably circumscribing a point of attachment of the trocar with the spacing member to provide stability and control over the positioning of the spacing member; and inserting said spacing member in an arcuate insertion path.

24. The method of claim 21, further comprising attaching a trocar to said spacing member.

25. A method of implanting an artificial intervertebral disc comprising:
(a) making an incision in an anulus of a human spinal column between adjacent vertebral bodies of said spinal column to thereby expose a space residing between said adjacent vertebral bodies;
(b) inserting a trial spacer through the incision and into position between the adjacent vertebral bodies, and evaluating a snugness of fit of said spacer as it resides between said adjacent vertebral bodies and determining a spacer size thereby, said trial spacer having sharp edging for clearing away tissue;
(c) selecting a spacing member having the spacer size determined in part (b) and inserting said spacing member through the incision and into position between the adjacent vertebral bodies.

26. The method of claim 25, wherein part (b) further comprises dislodging any unwanted soft tissue from between the vertebral bodies with the trial spacer.

27. The method of claim 25, further comprising inserting said trial spacer through the incision in an arcuate path.

28. The method of claim 25, further comprising positioning said spacing member at an anterior location with respect to the spinal column such that more intervertebral space resides posteriorly to said spacing member than anteriorly thereto.

29. The method of claim 25, further comprising applying compression to posterior portions of the adjacent vertebral bodies.

30. A method of implanting an artificial intervertebral disc comprising:
 (a) making an incision in an anulus of a human spinal column between adjacent vertebral bodies of said spinal column to thereby expose a space residing between said adjacent vertebral bodies, and inserting a trial spacer having sharp edging into the incision to clear away tissue from the incision;
 (b) inserting a spacing member through the incision and into position between the adjacent vertebral bodies, and positioning said spacing member at an anterior location with respect to the spinal column such that more intervertebral space resides posteriorly to said spacing member than anteriorly thereto;
 (c) applying compression to posterior portions of the adjacent vertebral bodies.

31. A method of implanting an artificial intervertebral disc comprising:
 (a) making an incision in an anulus of a human spinal column between adjacent vertebral bodies of said spinal column to thereby expose a space residing between said adjacent vertebral bodies;
 (b) inserting a spacing member through the incision and into position between the adjacent vertebral bodies, and positioning said spacing member at an anterior location with respect to the spinal column such that more intervertebral space resides posteriorly to said spacing member than anteriorly thereto;
 (c) applying compression to posterior portions of the adjacent vertebral bodies;
 wherein the method further comprises attaching an insertion instrument to said spacing member, wherein attaching an insertion instrument to said spacing member comprises threading a trocar on said spacing member, and further comprising supporting said spacing member with a hollow sheath member, said trocar being slidably disposed within said hollow sheath member, and further comprising abutting the sheath member against the spacing member and contactably circumscribing a point of attachment of the trocar with the spacing member to provide stability and control over the positioning of the spacing member.

32. A method of implanting an artificial intervertebral disc comprising:
 (a) making an incision in an anulus of a human spinal column between adjacent vertebral bodies of said spinal column to thereby expose a space residing between said adjacent vertebral bodies;
 (b) selecting a spacing member comprising an external concavo-convex contour with respect to one dimension of said spacing member, wherein the spacing member defines an imaginary arcuate centerline residing between opposing sides of the external concavo-convex contour of said spacing member, wherein the spacing member comprises an upper surface and a lower surface and a free insertion end, and wherein said spacing member includes a tapered portion such that said spacing member becomes progressively thinner toward said free insertion end of said spacing member;
 (c) inserting the spacing member along an arcuate insertion path through the incision such that the imaginary arcuate centerline follows said arcuate insertion path during the insertion; and
 (d) applying compression to posterior portions of the adjacent vertebral bodies.

* * * * *